United States Patent [19]

Chao et al.

[11] 4,283,560
[45] Aug. 11, 1981

[54] BULK CYCLOHEXANOL/CYCLOHEXANONE SEPARATION BY SELECTIVE ADSORPTION ON ZEOLITIC MOLECULAR SIEVES

[75] Inventors: Chien C. Chao, Millwood; John D. Sherman, Chappaqua, both of N.Y.

[73] Assignee: Union Carbide Corporation, New York, N.Y.

[21] Appl. No.: 98,714

[22] Filed: Nov. 30, 1979

[51] Int. Cl.³ ............................................ C07C 49/303
[52] U.S. Cl. ................................... 568/366; 568/835; 210/690; 252/455 Z
[58] Field of Search ............... 568/338, 366, 832, 835, 568/376; 423/328; 252/455 Z; 210/41, 690

[56] References Cited

U.S. PATENT DOCUMENTS

| | | | |
|---|---|---|---|
| 3,719,026 | 3/1973 | Sand | 252/455 Z |
| 3,732,326 | 5/1973 | Chen | 210/41 |
| 3,980,718 | 9/1976 | Shabtai et al. | 252/455 Z |

Primary Examiner—Natalie Trousof
Assistant Examiner—L. Hendriksen
Attorney, Agent, or Firm—Richard G. Miller

[57] ABSTRACT

Cyclohexanone is selectively adsorbed from admixture with cyclohexanol using specific cationic forms of zeolite X and zeolite Y. The process utilizes the interaction of the electrostatic field of the zeolite with the slightly greater polarity of the cyclohexanone to enhance the adsorptive strength difference between the competing adsorbates.

4 Claims, 1 Drawing Figure

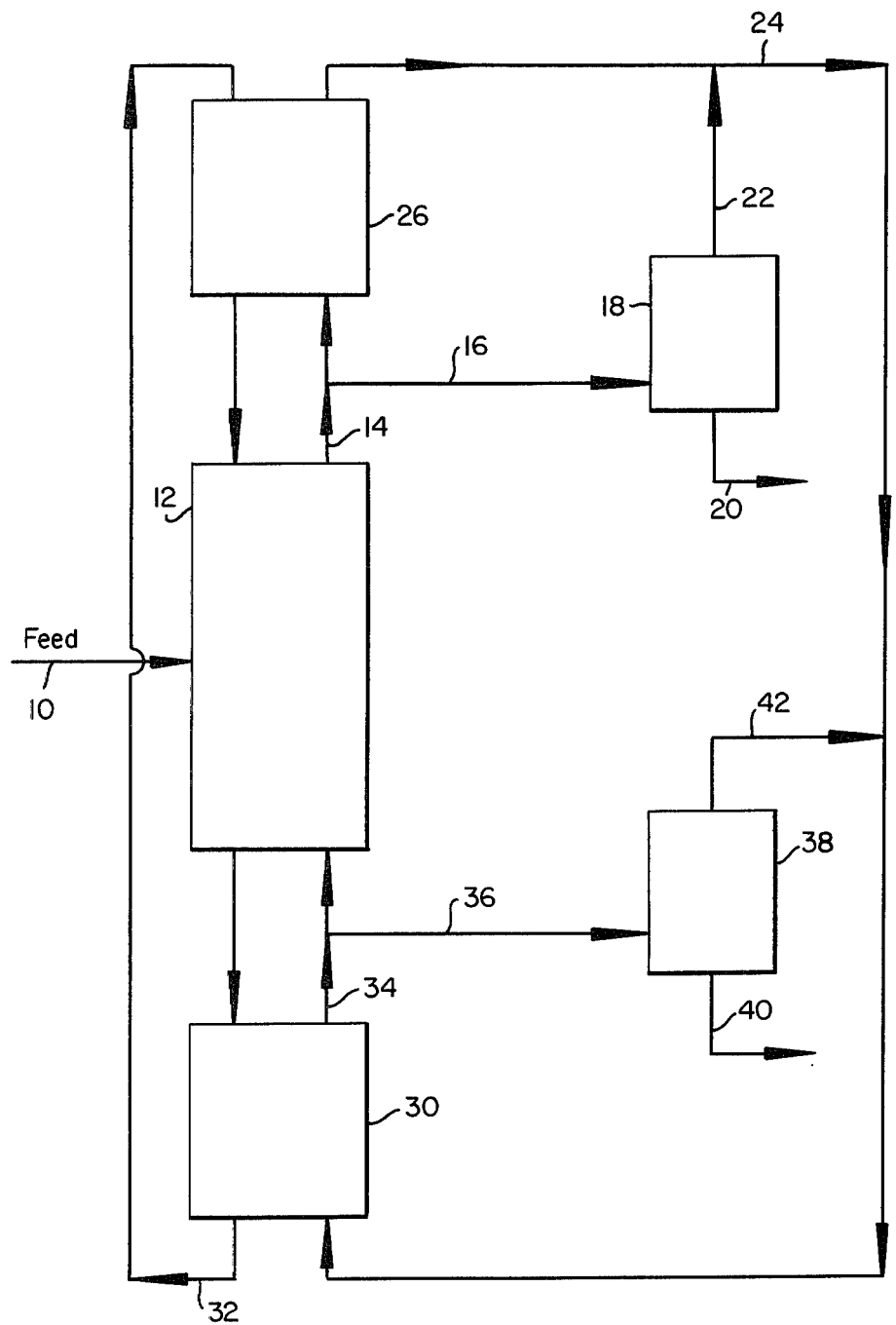

BULK CYCLOHEXANOL/CYCLOHEXANONE SEPARATION BY SELECTIVE ADSORPTION ON ZEOLITIC MOLECULAR SIEVES

The present invention relates in general to the bulk separation of mixtures of cyclohexanone and cyclohexanol, and more particularly to such a separation utilizing selective adsorption on certain types of zeolitic molecular sieves.

Cyclohexanone is a well known chemical widely used in the paint, varnish and plastics industry, particularly as a precursor of caprolactam used in the preparation of nylon polymers. On a commercial scale, cyclohexanone is most commonly synthesized either by the oxidation of cyclohexane, or by the hydrogenation of phenol. In such methods of preparation the cyclohexanone is always produced in admixture with substantial proportion of cyclohexanol. Product composition containing about 70 percent of cyclohexanone and 30 percent of cyclohexanol are typical.

Because cyclohexanol and cyclohexanone have normal boiling-points of 161.1° C. and 155.6° C., respectively, it has heretofore been found necessary to resort to vacuum distillation techniques to accomplish the required separation. Not only is the capital investment in the fractionation equipment quite substantial, but also the energy requirements to carry out the distillation are very large.

For a number of reasons separation of cyclohexanone and cyclohexanol by selective adsorption has not previously been either investigated thoroughly or been accomplished in a satisfactory manner. This is particularly so in the case of zeolitic molecular sieve adsorbents.

Firstly, adsorption selectivity based on molecular size, which is so commonly relied on in molecular sieve separations, is not as promising when it is considered that the molecular dimensions of cyclohexanone and cyclohexanol are very close. As measured using Fisher-Hirschfelder-Taylor molecular models, the dimensions of cyclohexanone are 4.7×6.5×7.0 Angstroms, whereas for cyclohexanol they are 5.0×6.5×8.0 Angstroms. This means that for the commercially available zeolite adsorbents which have pores large enough to adsorb even the smaller of the two molecular species, such as zeolite X and zeolite Y, no straight-forward selectivity based on molecular size would be exhibited, or even predicted.

Secondly, both cyclohexanol and cyclohexanone are polar molecules which may be adsorbed on large pore zeolites. Further, since cyclohexanone and cyclohexanol are both strongly adsorbed, and have very similar molecular dimensions which are of the same order of magnitude as the zeolite cages, kinetically controlled mass transfer in an adsorption bed pose could be expected serious problems.

From the foregoing consideration, it is apparent that the technology in this particular area of molecular sieve separation is in large part still empirical in nature, and that selectivity behavior is not readily predictable.

We have discovered, however, that cyclohexanone can in fact be separated from admixture with cyclohexanol by selective adsorption on molecular sieve zeolites by the process which comprises contacting a mixture comprising said compounds at a temperature of from 70° to 250° C. and a pressure sufficient to maintain the system in the liquid phase with an adsorbent composition comprising at least one crystalline aluminosilicate zeolite selected from the group consisting of zeolite X in which the zeolitic cations are predominantly calcium, barium, strontium, or a mixture of at least two thereof, and zeolite Y in which the zeolite cations are predominantly lithium, sodium, barium, or a mixture of at least two thereof, whereby cyclohexanone is selectively adsorbed thereon, removing the nonadsorbed portion of said mixture from contact with the zeolite adsorbent and desorbing the cyclohexanone adsorbate therefrom by contacting said adsorbent with a desorbing agent and recovering the desorbed cyclohexanone.

Zeolite X and the method for its manufacture are described in detail in U.S. Pat. No. 2,882,244 issued Apr. 14, 1959 to R. M. Milton. Zeolite Y and the method for its manufacture are described in detail in U.S. Pat. No. 3,130,007, issued Apr. 21, 1964 to D. W. Breck. The introduction of lithium, barium, strontium, potassium and calcium cations into the as-synthesized zeolite X and zeolite Y is readily accomplished using conventional ion-exchange techniques. It is preferred that the cation species recited above are associated with more than 50 percent of the $AlO_4$-tetrahedra of the zeolite, i.e. be more than the predominant cation species present. Advantageously at least about 70 percent of the $AlO_4$-tetrahedra are electrovalently satisfied by association with those specified cations.

We have determined that members of the foregoing groups of zeolite compositions exhibit a selectivity for cyclohexanone as compared with cyclohexanol under the conditions imposed on the present process. The selectivity is a result of the adsorption strength difference between cyclohexanone and cyclohexanol and is used to advantage in the present process to provide a separation. The adsorption potential is proportional to the electrostatic field strength of the zeolite adsorbent and to the polarity of the adsorbate molecule. In the present process the high electrostatic field of the zeolite is able to differentiate the small polarity differences of the competing adsorbates involved and create a large adsorption strength difference.

In evaluating the capabilities of the present process and in comparing it to other process systems, the adsorption selectivities of the adsorbates on various zeolites were determined by a "shake test". This test consisted of a procedure carried out at 25° C. using a test solution containing 5 weight-percent of each of cyclohexanone and cyclohexanol and 90 weight-percent of 2, 2, 4-trimethylpentane. Crystals of the zeolite to be tested were added to portions of the test solution in a sealed container and the system agitated for 16 hours. Thereafter the liquid phase was analyzed to determine the weight percentage of cyclohexanone and/or cyclohexanol adsorbed by the zeolite. From these data the selectivity factor (S.F.), OC (-one/-ol), was calculated in accordance with the following equation:

$$S.F. = \alpha \frac{\text{-one}}{\text{-ol}} = \frac{[\text{conc. } A/\text{conc. } B] \text{ (adsorbed phase)}}{[\text{conc. } A/\text{conc. } B] \text{ (liquid phase)}},$$

wherein A represents cyclohexanone and B represents cyclohexanol. The selectivity factor values for a number of zeolite compositions are set forth in Table A, below. An $\alpha$-value of greater than unity indicates that the particular adsorbent tended to be cyclohexanone-selective under the test conditions employed.

TABLE A

| Zeolite | Selectivity Factor, $\frac{\text{-one}}{\text{-ol}}$ |
|---|---|
| H$^+$-ZSM-5-Type[a] | 0.24[b] |
| UHP-Y[c] | 0.56 |
| Li-X | 2.4 |
| Na-X | 1.2 |
| K-X | 0.55[b] |
| Cs-X | 1.2 |
| Ca-X | 43.[b] |
| Sr-X | 9.5 |
| Ba-X | 5.5[b] |
| Li-Y | 8.0 |
| Na-Y | 53.[b] |
| K-Y | 1.3 |
| Cs-Y | 1.5 |
| Ca-Y | 3.0[d] |
| Sr-Y | 4.2 |
| Ba-Y | 7.7 |

[a] Calcined and acid washed ZSM-5-Type (U.S. Pat. No. 3,702,886, issued November 14, 1972).
[b] Average of two values.
[c] Hydrophobic derivative of zeolite Y: U.S. Ser. No. 880,561 filed February 23, 1978.
[d] Average of three values; not fully reproducible results, suggesting interaction or catalytic effects.

It is apparent from the data of Table A that the barium, strontium and calcium forms of zeolite X and the lithium, sodium, and barium forms of zeolite Y are cyclohexanone-selective, with Na-Y and Ca-X being outstanding in this regard. Surprisingly, K-X was found to be cyclohexanol-selective whereas K-Y tended to be cyclohexanone-selective. Also, in the case of Ca-X and Ca-Y, the former has excellent selectivity for cyclohexanone, but the latter appears to be much less selective for cyclohexanone; its behavior may be due to interaction effects. Ca-Y, moreover, is highly active as a catalyst in the conversion of cyclohexanol—a highly undesirable property in the present process—whereas Ca-X is more suitable in this regard, at least at temperatures within the scope of the present process.

In separating cyclohexanone and cyclohexanol in the present process, a bed of solid zeolite adsorbent is contacted with a feed mixture, the cyclohexanone is preferentially adsorbed on the adsorbent, the unadsorbed or raffinate mixture is removed from the adsorbent bed, and the adsorbed cyclohexanone is desorbed from the zeolite adsorbent. The adsorbent can, if desired, be contained in a single bed, a plurality of beds in which conventional swing-bed operation techniques are utilized, or a simulated moving-bed countercurrent type of apparatus. The preferred mode of operation is the simulated moving-bed technique such as that described in U.S. Pat. No. 2,985,589 issued May 23, 1961 to D. B. Broughton et al. In this method of operation, the selection of a suitable displacing or desorbing agent or fluid (solvent) must take into account the requirements that it be capable of readily displacing adsorbed cycylohexanone from the adsorbent bed and also that cyclohexanone from the feed mixture be able to displace adsorbed desorbing agent from a previous desorption step. Further, the solvent should be selected in view of the particular zeolite adsorbent composition employed and also the feedstock being treated, since certain desorbing solvents can react inter se and with the feedstock molecules due to the catalytic activity of the zeolite and/or binder components thereof. Still further, the desorbing agent employed should be readily separable from admixture with the cyclohexanone and cyclohexanol components of the feedstock. Therefore it is contemplated that a desorbing agent having a different boiling range than the feedstock be utilized, thus allowing thermal fractionation methods to be used to separate such desorbing agent from the feedstock components.

Desorbing agents which can be used in the present process include various partially oxygenated hydrocarbons such as tetrahydrofuran, ethylacetate, methylacetate, linear primary $C_3$-$C_5$ alcohols and $C_3$-$C_4$ ketones.

Of the particular above-enumerated zeolites, Na-Y is found to have the highest selectivity for cyclohexanone and to impart no serious rate (diffusion) or catalytic problems to the separation process. Accordingly this zeolite is a preferred species, particularly when the desorbing material used is either tetrahydrofuran or ethylacetate. The adsorption properties of the former is especially compatible with the corresponding properties of cyclohexanone and cyclohexanol, and the latter, in addition to having excellent adsorptive properties for the present process, actually appears to inhibit reactivity of cyclohexanol and cyclohexanone in contact with the zeolite.

It is much preferred that the feedstock is substantially all cyclohexanone and cyclohexanol with only normal impurity levels of other constituents. The adsorption characteristics of other components with respect to the zeolite adsorbent involved must be taken into account if appreciable amounts of impurities are present. The relative concentrations of cyclohexanol and cyclohexanone with respect to each other is not a narrowly critical factor, but it is advantageous if the mixture contains at least 10 mole-percent of either form.

While it is possible to utilize the activated adsorbent zeolite crystals in a non-agglomerated form, it is generally more feasible, particularly when the process involves the use of a fixed adsorption bed, to agglomerate the crystals into larger particles to decrease the pressure drop in the system. The particular agglomerating agent and the agglomeration procedure employed are not critical factors, but it is important that the bonding agent be as inert toward the cyclohexanone, cyclohexanol and the desorbing agent as possible. It also should be as low in catalytic activity toward those compounds as is possible. As a general class, clay binders are suitable, but it is found that bentonite-type clays exhibit less catalytic activity, particularly toward polymerization-type reactions, than others of the class which include attapulgite, kaolin, sepiolite, palygorskite, montmorillonite, illite and chlorite. The proportions of zeolite and clay are advantageously in the range of 4 to 10 parts zeolite per part clay on an anhydrous weight basis.

The temperature at which the adsorption step of the process is carried out must be within the range of 70° to 250° C. It has been found that at temperatures below about 50° C. the counter-diffusion rate between cyclohexanol and cyclohexanone is too slow, i.e., a sufficient selectivity for the cyclohexanone is not exhibited by the zeolite. Above about 250° C., the undesirable catalytic activity of the zeolite can become appreciable. Also, pressure conditions must be increased with increasing temperature to maintain the system in the liquid phase, and accordingly, high process temperatures needlessly necessitate high pressure apparatus with the attendant increase in apparatus costs.

In the drawings the FIGURE represents a hypothetical simulated moving-bed countercurrent flow diagram involved in carrying out a typical process embodiment of the present invention.

With reference to the drawing, it will be understood that whereas the liquid stream inlets and outlets are represented as being fixed, and the adsorbent mass is represented as moving with respect to the counterflow of feedstock and desorbing material, this representation is intended primarily to facilitate describing the functioning of the system. In practice the sorbent mass would ordinarily be in a fixed bed with the liquid stream inlets and outlets moving with respect thereto. Accordingly, a feedstock consisting essentially of a mixture of 70 mole-percent cyclohexanone and 30 mole-percent cyclohexanol is fed into the system through line 10 to adsorbent bed 12 which contains particles of activated sodium zeolite Y (Na-Y) adsorbent in transit downwardly therethrough. The temperature is 125°–150° C. throughout the entire system and the pressure is substantially 100 psia. The cyclohexanone component of the feedstock is adsorbed preferentially on the zeolite particles moving through bed 12, and the raffinate cyclohexanol is entrained in the liquid stream of ethylacetate desorbing agent which flows upwardly through bed 12. This liquid mixture of the cyclohexanol component and the desorbing agent leave bed 12 through line 14 and a major portion thereof is withdrawn through line 16 and fed into distillation apparatus 18 wherein the mixture is fractionated and the cyclohexanol is discharged through line 20 as a purified product. The ethylacetate desorbing agent leaves the distillation apparatus 18 through line 22 and is fed to line 24 through which it is admixed with additional desorbing agent leaving the adsorbent bed 26, and is recycled to the bottom of adsorbent bed 30. The zeolite Na-Y carrying adsorbed cyclohexanone passes downward through line into bed 30 where it is countercurrently contacted with recycled desorbing agent which effectively desorbs the cyclohexanone therefrom before the adsorbent passes through bed 30 and enters line 32 through which it is recycled to the top of adsorbent bed 26. The desorbing agent and desorbed cyclohexanone leave bed 30 through line 34. A portion of this liquid mixture is diverted through line 36, where it passes to distillation apparatus 38, and the remaining portion passes upward through adsorbent bed 12 wherein it becomes admixed with substantial amounts of cyclohexanol before exiting through line 14 for further treatment as hereinbefore described. In distillation apparatus 38, the desorbing agent and cyclohexanone are fractionated. The cyclohexanone product is recovered through line 40 and the desorbing agent passes through line 42 into line 24 for recycle as described above. The undiverted portion of the desorbing agent—cyclohexanol mixture passes from bed 12 through line 14 enters bed 26 and moves countercurrently upward therethrough with respect to the desorbing agent—laden zeolite adsorbent passing downwardly therethrough from recycle line 32. The desorbing agent passes from bed 26 in a relatively pure form through recycle line 24 to bed 30 as hereinbefore described.

What is claimed is:

1. Process for separating cyclohexanone from admixture with cyclohexanol by selective adsorption which comprises contacting a mixture comprising said compounds at a temperature of from 70° to 250° C. and at a pressure sufficient to maintain the system in the liquid phase with an adsorbent composition comprising at least one crystalline aluminosilicate zeolite selected from the group consisting of zeolite X in which the zeolitic cations are predominantly calcium, barium, strontium, or a mixture of at least two thereof, and zeolite Y in which the zeolitic cations are predominantly lithium, sodium, barium, or a mixture of at least two thereof, whereby cyclohexanone is selectively adsorbed thereon, removing the non-adsorbed portion of said mixture from contact with the zeolite adsorbent and desorbing the cyclohexanone adsorbate therefrom by contacting said adsorbent with a desorbing agent and recovering the desorbed cyclohexanone.

2. Process according to claim 1 wherein the crystalline aluminosilicate zeolite adsorbent is sodium zeolite Y.

3. Process according to claim 2 wherein the desorbing agent is tetrahydrofuran.

4. Process according to claim 2 wherein the desorbing agent is ethylacetate.

* * * * *